United States Patent [19]

Baumel

[11] Patent Number: 5,046,368

[45] Date of Patent: Sep. 10, 1991

[54] APPARATUS AND METHOD FOR FATIGUE TESTING A WHEEL

[76] Inventor: Stanley J. Baumel, 3400 Lagoon Dr., Burlington, Wis. 53105

[21] Appl. No.: 606,148

[22] Filed: Oct. 31, 1990

Related U.S. Application Data

[63] Continuation-in-part of Ser. No. 443,217, Nov. 29, 1989, Pat. No. 4,998,440.

[51] Int. Cl.⁵ .............................................. G01N 3/32
[52] U.S. Cl. .................................................... 73/810
[58] Field of Search ................ 73/810, 812, 849, 851, 73/118.1; 157/16, 17, 21; 82/104; 408/106; 29/894

[56] References Cited

U.S. PATENT DOCUMENTS 2,761,310  9/1956  Siegel ................................ 73/812 X
2,953,018  9/1960  Volmer ................................ 73/812

FOREIGN PATENT DOCUMENTS 36001  2/1990  Japan ................................ 82/104

Primary Examiner—Jerry W. Myracle
Attorney, Agent, or Firm—Andrus, Sceales, Starke & Sawall

[57] ABSTRACT

An apparatus and method for fatigue stress testing a vehicle wheel or the like includes a plate to which the wheel is mounted, and a clamping system for maintaining the wheel stationary. The clamping system fixes the vertical and lateral position of both the upper and lower lips of the wheel, to replicate operating conditions. A nonrotatable shaft is connected to the plate through a bushing. The shaft is connected at a point spaced from the plate to a rotating lateral loading assembly, which rotates relative to the shaft. The lateral loading assembly exerts a lateral force on the shaft simultaneous with rotation of the assembly, so as to cause wobbling of the shaft, which is transferred through the stress plate to the wheel.

13 Claims, 3 Drawing Sheets

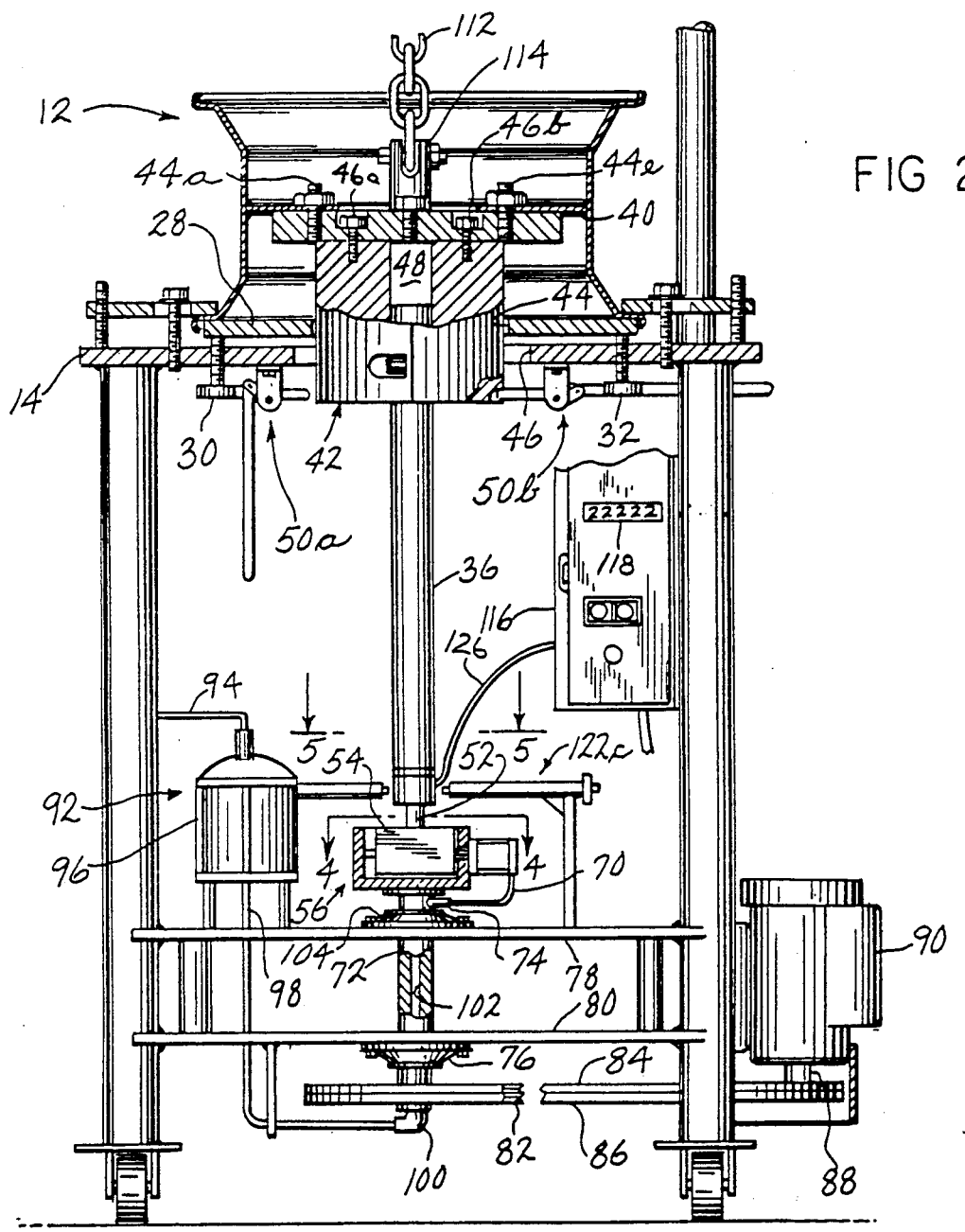

APPARATUS AND METHOD FOR FATIGUE TESTING A WHEEL

CROSS-REFERENCE TO RELATED APPLICATION

This application is a continuation-in-part of application Ser. No. 07/443,217 filed Nov. 29, 1989, now U.S, Pat. No. 4,998,440.

BACKGROUND AND SUMMARY

This invention relates to an apparatus and method for fatigue testing a vehicle wheel, such as is required of high performance racing wheels.

Fatique testing of vehicle wheels is frequently performed by wheel manufacturers to ascertain the number of revolutions the wheel can withstand before failing when a predetermined moment is applied to the wheel. Many of the organizations which govern a particular type of racing set standards for fatigue testing which must be met by a manufacturer's wheels before they can be used in that type of racing.

In the past, machines for fatigue testing vehicle wheels have simulated the action of the wheel on the vehicle. The wheel is mounted to a plate and a predetermined moment is exerted on the plate through a shaft mounted to the plate. The wheel is then spun about an axis coincident with the longitudinal axis of the shaft, which replicates stresses experienced by a wheel as mounted to a vehicle during operation of the vehicle.

The present invention provides an apparatus and method for fatigue testing a vehicle wheel, which also simulates the stresses experienced by a wheel as mounted to a vehicle. In direct contrast to the known testing procedure and apparatus, however, the present invention maintains the wheel stationary during testing. This allows the wheel to be observed and monitored during the test, which may reveal to the manufacturer certain areas of weakness in the wheel not detectable during a test in which the wheel is spun.

In accordance with the invention, an apparatus for fatigue testing vehicle wheel comprises wheel support means for maintaining the wheel stationary, and fatigue stress inducing means connected to the wheel for inducing stress in the wheel so as to simulate stress induced in the wheel when the wheel is mounted to a vehicle.

The wheel support means includes first support means engageable with one side of the wheel inwardly of a first lip of the wheel, and second support means engageable with the other side of the wheel inwardly of a second lip of the wheel. The first and second support means cooperate to fix the vertical and lateral position of the wheel on the apparatus during testing. The first support means comprises wheel supporting plate member which is preferably dimensioned so as to fit within the interior of an outwardly facing recess defined by the first lip of the wheel. A clamping assembly is provided for clamping the lower lip of the wheel to the wheel supporting plate member. The second support means preferably comprises a series of radially spaced clamping assemblies engageable with the wheel adjacent the upper lip of the wheel. In one embodiment, each clamping assembly comprises a lower support plate engageable with an inner surface of the wheel adjacent the upper lip of the wheel, and a threaded clamping member movable toward and away from the lower support plate and engageable with an outer surface of the wheel adjacent the upper lip. Each clamping assembly is preferably mounted to a collar member, which is mounted for vertical movement to a post. The collar members are provided with locking means for selectively fixing their vertical position on the posts.

The fatigue stress inducing means comprises a stress plate to which the wheel is bolted by means of bolt-receiving openings provided in the wheel, and a non-rotatable shaft extending from and interconnected with the stress plate. At least a portion of the shaft is mounted to a lateral loading assembly, which is rotatable relative to the shaft. The lateral loading assembly exerts a force on the shaft in a direction other than in line with the longitudinal axis of the shaft, and preferably in a direction substantially perpendicular thereto. In a preferred embodiment, the lateral loading assembly comprises a bearing member into which at least a portion of the shaft extends, lateral loading means exerting a lateral force on the bearing member which causes the bearing member to move laterally relative to the shaft, and means for imparting rotation to the bearing member when the lateral force is exerted on the bearing member. When the lateral force is exerted on the shaft and the lateral loading assembly is rotated, the shaft is caused to "wobble", which action is transferred through the shaft to the stress plate. Wobbling of the stress plate simulates the relationship of the wheel to a vehicle when the wheel is mounted to the vehicle and the vehicle is operated. The lateral force on the shaft is continuously exerted while the lateral loading assembly rotates so that, in time, the wheel fails due to fatigue loading. Based on the number of revolutions of the lateral loading assembly, the wheel manufacturer can determine whether the wheel conforms to the desired standards.

In a preferred embodiment, the lateral loading assembly comprises a bearing member mounted for slidable lateral movement within a carriage assembly. The carriage assembly is connected to the rotation imparting means for rotating the bearing member. A fluid-operated cylinder assembly is mounted to the carriage assembly, which is operable to selectively exert a lateral force on the bearing assembly. The exertion of a lateral force on the bearing assembly causes the bearing assembly to slide laterally within the carriage assembly, and to laterally deflect the portion of the shaft connected to the bearing assembly due to yielding of the wheel. In a particularly satisfactory construction, fluid pressure is supplied to the fluid-operated cylinder assembly through an internal passage provided in a shaft to which the carriage assembly is connected. A motor or the like is connected to the shaft for imparting rotation thereto, which is transferred through the shaft to the carriage assembly. A conduit extends between the shaft adjacent the carriage assembly and the fluid-operated cylinder for supplying fluid pressure to the cylinder.

Disabling means is preferably provided for disabling the apparatus when a predetermined amount of deflection of the shaft occurs, which corresponds to failure of the wheel.

In the preferred embodiment as described above, the fatigue stress inducing assembly is connected to the wheel and depends from the wheel. Counterweight means is preferably provided for offsetting the weight of the fatigue stress inducing assembly to reduce the effect thereof on the wheel during testing. As summarized above, the fatigue stress inducing assembly includes a stress plate to which the wheel is mountable. The wheel preferably includes a substantially central opening, and the counterweight means includes means for exerting an upward force on the stress plate through the opening in the wheel, with the upward force offsetting the weight of the fatigue stress inducing assembly. In one embodiment, a lug is mounted to the plate and extends through the opening in the wheel, and the upward force is exerted on the plate through the lug. The upward force exerting means includes a cylinder assembly having a movable piston, which is connected to the lug through a flexible connector member, such as a chain or cable. Retraction of the piston results in an upward force exerted on the lug through the chain or cable.

The invention also contemplates a method of fatigue testing a wheel, substantially in accordance with the foregoing description.

BRIEF DESCRIPTION OF THE DRAWINGS

The drawings illustrate the best mode presently contemplated of carrying out the invention.

In the drawings:

FIG. 2 is a side elevation view, with portions in section, showing the fatigue testing apparatus of FIG. 1;

FIG. 4 is a partial sectional view taken generally along line 4—4 of FIG. 2;

FIG. 5 is a partial sectional view taken generally along line 5—5 of FIG. 2;

DETAILED DESCRIPTION OF THE PREFERRED EMBODIMENT

Figure 1:
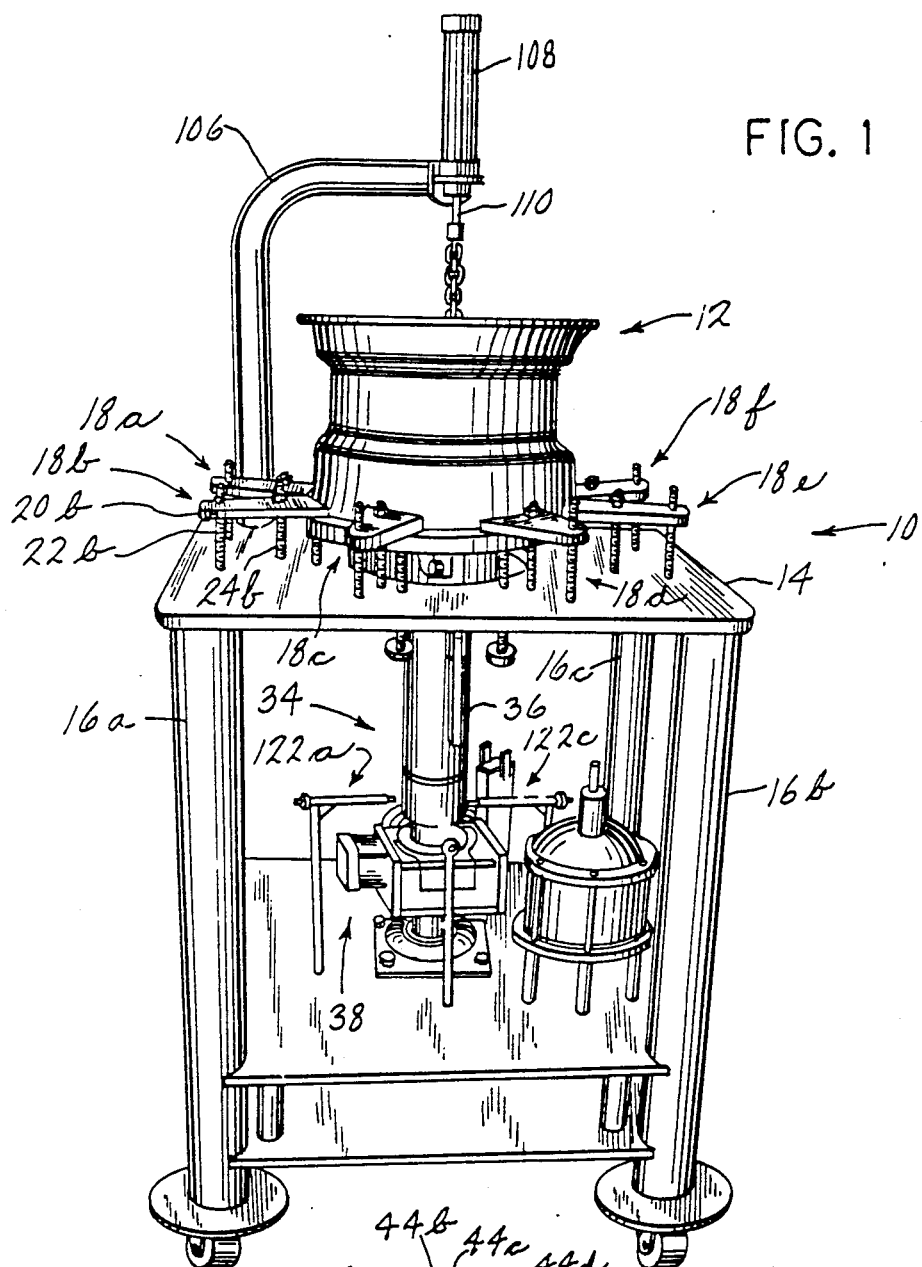
FIG. 1 is a perspective view of the wheel fatigue testing apparatus of the invention, showing a wheel mounted thereto.

As illustrated in FIG. 1, a wheel fatigue testing apparatus, shown at 10, is provided for fatigue testing a vehicle wheel, shown at 12. Wheel 12 as illustrated is a high performance racing wheel, but it is understood that apparatus 10 may be used to test any vehicle wheel or the like which is subjected to rotation during operation and which experiences stresses caused by exertion of a lateral load offset from the wheel.

Apparatus 10 generally includes a wheel clamping stand including a planar upper member 14 and a series of depending legs shown at 16a, 16b, 16c and 16d. Casters are provided at the lower ends of legs 16a–16d for providing movability of apparatus 10.

A series of clamping members 18a, 18b, 18c, 18d, 18e and 18f are connected to upper member 14. Referring to clamping member 18b, each of clamping members 18a–18f includes a clamping plate, such as shown at 20b, a threaded spacer such as shown at 22b, and a clamping bolt such as 24b fitted with a nut toward its upper end.

Figure 3:
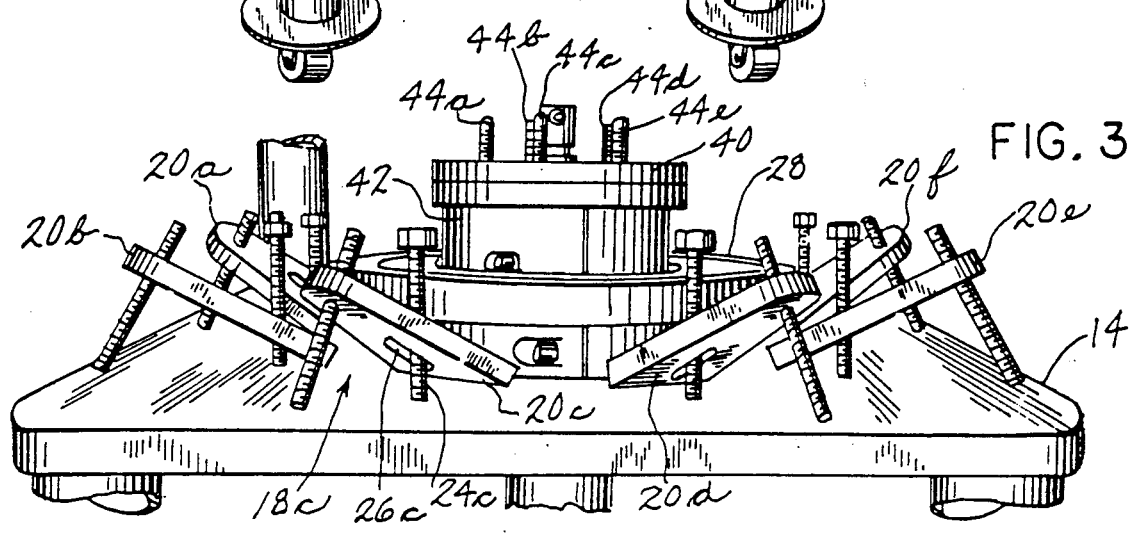
FIG. 3 is a partial perspective view showing the upper portion of the fatigue testing apparatus of FIG. 1, with the wheel removed.

Referring to FIG. 3, clamping members 18a–18f are shown in their disengaged position, wherein wheel 12 is removed from apparatus 10. In FIG. 3, it is seen that each of the clamping bolts, such as shown at 24c, extend through slots such as shown at 26c, provided in the clamping plates, such as shown at 20c. With this arrangement, the clamping plates are movable in an inward and outward manner on the clamping bolts, for accommodating various sizes of wheels mounted to apparatus 10.

As also shown in FIG. 3, a wheel supporting plate 28 is connected to and supported by upper member 14. As shown in FIG. 2, wheel 12 is mounted to upper member 14 of apparatus 10 by placing wheel 12 on wheel supporting plate 28. Clamping members 18a–18f are then positioned such that the inwardly facing ends of the clamping plates are positioned against wheel 12, with the horizontal portion of wheel 12 sandwiched between the lower surface of each clamping plate and the upper surface of wheel supporting plate 28. The nuts provided on each of the clamping bolts are then turned down, so as to clamp the rim of wheel 12 to upper member 14.

As also shown in FIG. 2, a series of height adjusting screws, such as shown at 30, 32, support wheel supporting plate 28 above the upper surface of upper member 14. Height adjusting screws 30, 32 allow wheels of varying depths to be satisfactorily mounted to apparatus 10.

Referring to FIG. 1, a fatigue stress inducing assembly 34 extends below upper member 14. Assembly 34 consists generally of a nonrotatable shaft 36, a rotatable lateral loading assembly 38, and a stress plate 40 (FIGS. 2, 3). Stress plate 40 is connected to a conventional split bushing 42, which is disposed between shaft 36 and stress plate 40.

Stress plate 40 is mounted to the hub of wheel 12 in a manner similar to that in which wheel 12 is mounted to a vehicle. Stress plate 40 is provided with a series of upstanding bolts, such as shown at 44a, 44b, 44c, 44d and 44e (FIG. 3). Bolts 44a–44e are arranged in a predetermined bolt pattern corresponding to the pattern of the openings in the hub of wheel 12. As shown in FIG. 3, bolts 44a–44e are arranged in a relatively small diameter pattern. Referring to FIG. 2, however, a somewhat larger stress plate 40 is shown, incorporating bolts such as shown at 44a, 44e in a larger diameter bolt pattern for testing a wheel having a corresponding bolt pattern.

Stress plate 40 is connected to bushing 42 by a series of threaded bolts, such as shown at 46a, 46b in FIG. 2. As shown, bushing 42 extends through an opening 44 formed in wheel supporting plate 28, and an opening 46 formed in upper member 14.

Shaft 36 extends upwardly into a central passage 48 formed in bushing 42, and terminates at a point below the lower surface of stress plate 40.

A series of toggle clamps, two of which are shown at 50a, 50b, are connected to the underside of upper member 14. Toggle clamps 50a, 50b are movable between a release position, in which clamp 50a is shown, and a clamping position, in which clamp 50b is shown. While two toggle clamps are illustrated, it is preferable that four such clamps are provided at equal radial spacing about the outer periphery of bushing 42. Such clamps act to center bushing 42 during operation of apparatus 10.

The lower end of shaft 36 is provided with a reduced diameter extension portion, shown at 52. As shown in FIGS. 2 and 4, extension portion 52 mates with a female opening provided in a modified pillow block bearing member 54.

Pillow block bearing member 54 is mounted for slidable back and forth movement in a carriage assembly, shown at 56. Carriage assembly 56 comprises a bottom plate member and a series of upstanding walls extending therefrom. Referring to FIG. 4, bearing member 54 is slidably mounted to carriage assembly 56 by means of a pair of gibs shown at 58, 60 which extend inwardly from opposed side walls of carriage assembly 56. A pair of mating slots are formed in the side walls of bearing member 54 adjacent the carriage assembly side walls on which gibs 58, 60 are formed. A centering bolt 62 is provided in a threaded opening formed in an end wall of carriage assembly 56. Centering bolt 62 is adpated to engage bearing member 54 when turned down so as to move rightwardly, to center bearing member 54 relative to shaft 36. After bearing member 54 is centered in this manner, centering bolt 62 is turned so as to move leftwardly, thereby allowing sliding movement of bearing member 54 within carriage assembly 56.

A hydraulic cylinder assembly, shown at 64, is mounted to the end wall of carriage assembly 56 opposite centering screw 62. Cylinder assembly 64 includes an extendible and retractable piston member including a piston rod 66, which extends through an opening 68 formed in the end wall of carriage assembly 56 to which cylinder assembly 64 is mounted. Piston rod 66 is extendible upon supply of hydraulic pressure through a hydraulic line 70 to cylinder assembly 64, for moving piston rod 66 leftwardly. Such movement of piston rod 66 exerts a lateral force on the lower end of shaft 36, which is transferred through bushings 42 and stress plate 40 to the hub of wheel 12. This causes the hub of wheel 12 to yield, which results in sliding movement of bearing member 54 within carriage assembly 56, to a leftward position shown in FIG. 4 in phantom. Turning centering screw 62 so that it moves rightwardly causes bearing assembly 54 to return to its rightwardmost position, and retraction of piston rod 66 within cylinder assembly 64.

Referring to FIG. 2, carriage assembly 56 is mounted to the upper end of a shaft 72, which is rotatably supported by a pair of bearing assemblies 74, 76 mounted to plates 78, 80, respectively. A driven pulley 82 is mounted to the lower end of shaft 72, and a pair of V-belts 84, 86 are trained about pulley 82 and a drive pulley connected to the output shaft 88 of an electric motor 90. In a know manner, operation of motor 90 drives belts 84, 86 and pulley 82, thereby imparting rotation to shaft 72. Such rotation of shaft 72 causes rotation of carriage assembly 56.

A hydraulic pressure source, shown at 92, is mounted to the upper surface of plate 78. Hydraulic pressure source 92 is preferably an air over hydraulic system; in which pressurized air is supplied through an air line 94 to a body portion 96. An outlet line 98 extends from body portion 96, and transfers hydraulic fluid pressure therefrom in response to the supply of pressurized air. Line 98 is connected to a rotary valve 100, which is in communication with an internal central passage 102 formed in shaft 72. In this manner, supply of hydraulic fluid pressure from line 98 through valve 100 is transferred through passage 102, and through a fitting 104 which communicates such fluid pressure from internal passage 102 to hydraulic line 70 interconnected with cylinder assembly 64. With this arrangement, hydraulic fluid pressure is supplied to hydraulic cylinder assembly 64 while carriage assembly 56 and hydraulic cylinder assembly 64 are being rotated by the drive arrangement described above.

Alternatively, the air over hydraulic system may be replaced with an entirely pneumatic system including an accumulator, which eliminates pressure fluctuations which may result from employing hydraulic fluid pressure.

Referring to FIGS. 1 and 2, an upstanding arm 106 extends above upper member 14. A pneumatic cylinder assembly 108 is connected to the end of arm 106, and includes an extendible and retractable piston rod 110. Piston rod 110 is connected to the upper end of a multi-link chain 112, which is connected at its lower end to a lug 114 attached to the upper surface of stress plate 40. Upon supply of air pressure to pneumatic cylinder assembly 108 so as to cause retraction of piston rod 110, an upward force is exerted on stress plate 40 through lug 114 and chain 112. The amount of the upward force exerted on stress plate 40 through chain 112 is approximately equal to the weight of the components which are suspended from the hub of wheel 12, namely stress plate 40, bushing 42 and shaft 36. In this manner, the weight of such components does not affect the stress induced in wheel 12 during operation of apparatus 10.

In operation, apparatus 10 functions as follows. Wheel 12 is first positioned on wheel supporting plate 28 and clamped thereto by means of clamping members 18a–18f. The hub of wheel 12 is bolted to stress plate 40 by means of bolts such as 44a, 44e extending upwardly from stress plate 40. Centering pin 62 is turned into carriage assembly 56 so as to cause bearing member 54 to assume its full rightwardmost position within carriage assembly 56, shown in solid lines in FIG. 4. Centering bolt 62 is then moved leftwardly out of engagement with bearing member 54, in an amount sufficient to allow full leftward movement of bearing member 54 within carriage assembly 56. Through a control panel 116 (FIG. 2), motor 90 is actuated so as to impart rotation to shaft 72 through the pulley and belt drive system. This rotation of shaft 72 causes rotation of carriage assembly 56 and hydraulic cylinder assembly 64. Extension portion 52 of shaft 36 is disposed within the bearing passage of bearing member 54, and accordingly no rotation is imparted to shaft 36. When it is desired to initiate the fatigue stress test of wheel 12, a button on panel 116 is depressed so as to actuate an air compressor (not shown), which supplies pressurized air through air line 94 to hydraulic pressure source 92. This results in the output of fluid pressure from hydraulic pressure source 92, through line 98. The pressurized fluid flows through rotary valve 100 and central passage 102 formed in shaft 72, through fitting 104 and hydraulic line 70 to hydraulic cylinder assembly 64. In a known manner, such supply of hydraulic fluid pressure to hydraulic cylinder assembly 64 causes extension of piston rod 66 associated therewith. Appropriate hydraulic valving is provided so that a predetermined force is exerted through piston rod 66 on bearing member 54. The force exerted on bearing member 54 by piston rod 66 causes bearing member 54 to slide leftwardly within carriage assembly 56 due to yielding of the hub of wheel 12, so that the center of extension portion 52 of shaft 36 is moved leftwardly relative to its original position. The leftward position of extension portion 52 is shown in phantom in FIG. 4. When this occurs, and carriage assembly 56 continues to be rotated, a rotating lateral force is exerted on shaft 36 at extension portion 52. This rotating lateral force causes shaft 36 to wobble, which action is transferred through bushing 42 to stress plate 40, and accordingly to the hub of wheel 12. Control panel 116 includes a counter, shown at 118, which counts the revolutions of carriage assembly 56. In this manner, it can be ascertained how many revolutions of carriage assembly 56 take place before fatigue stress failure of wheel 12 induced by stress plate 40.

When wheel 12 begins to fail, the force exerted on extension portion 52 of shaft 36 by piston rod 66 will cause additional leftward sliding movement of bearing member 54 in carriage assembly 56. When this occurs, a disabling mechanism is provided for shutting down apparatus 10 when the lower end of shaft 36 moves laterally an amount sufficient to indicate failure of wheel 12. This mechanism comprises a series of sensors, shown in FIGS. 1, 2 and 5 at 122a, 122b, 122c and 122d. Each of sensors 122a-122d includes a contact member 124a, 124b, 124c and 124d, respectively. Contact members 124a-124d are wired into a disabling circuit, which is capable of shutting down motor 90. An electrical lead 126, which is interconnected with the disabling circuit, extends between control panel 116 and the lower end of shaft 36 immediately above extension portion 52. Electrical lead 126 supplies an electrical potential to the lower portion of shaft 36. Each of contact members 124a-124d is also supplied with an electrical potential. When wheel 12 fails and the lower end of shaft 36 begins to deflect a sufficient amount so as to cause the outer surface of shaft 36 to come into contact with contact members 124a-124d upon rotation of carriage assembly 56, such contact completes the diabling circuit so as to shut down motor 90. In this manner, the system can be left unattended, while counter 118 provides an accurate count of revolutions prior to failure of wheel 12.

Figure 6:
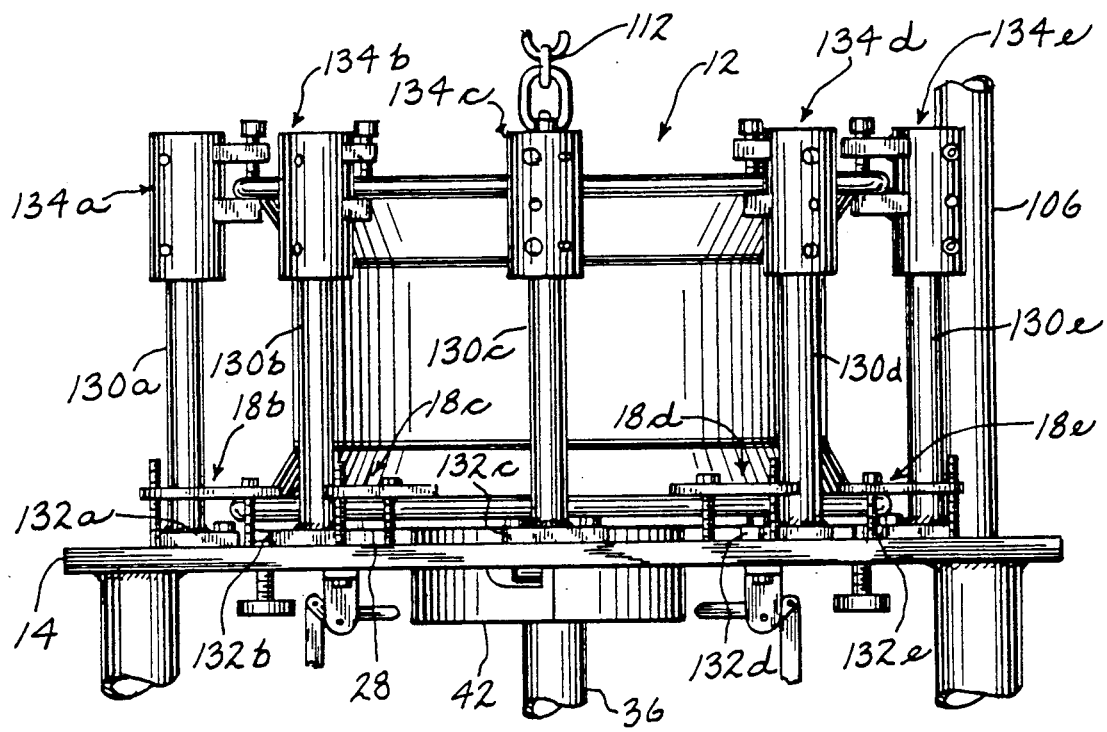
FIG. 6 is a partial side elevation view of the upper portion of the fatigue testing apparatus, showing an alternate embodiment for clamping the upper portion of the wheel.
Figure 7:
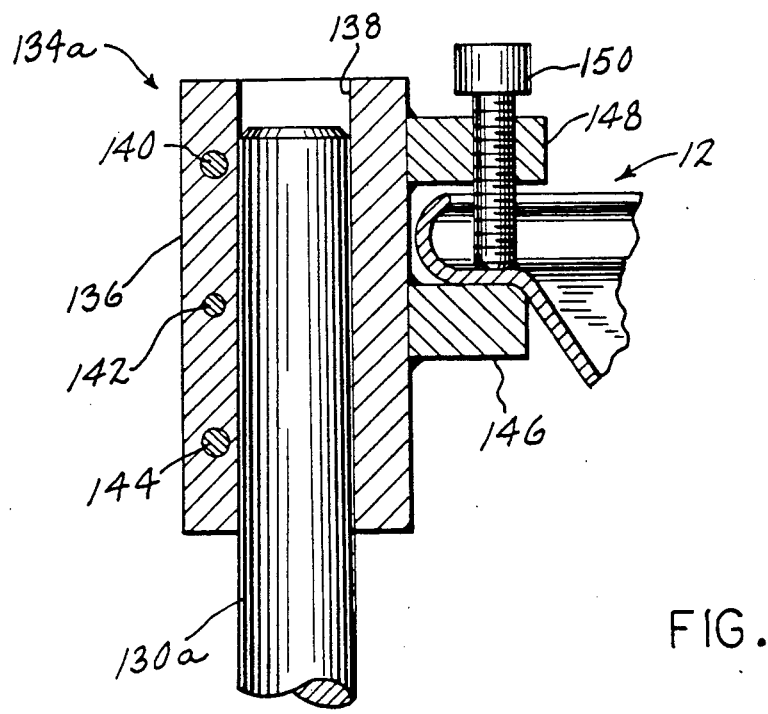
FIG. 7 is an enlarged partial sectional view showing clamping of the upper portion of the wheel.

Another arrangement for clamping of wheel 12 is shown in FIGS. 6 and 7. A series of posts, such as shown at 130a, 130b, 130c, 130d and 130e, are connected to the upper surface of upper member 14 through a series of plates 132a-132e, respectively, bolted to upper member 14. Posts 130a-130e are radially spaced around the periphery of the area in which wheel 12 is adapted to be received.

A clamping assembly is provided on each of the posts, such as 130a-130e, with the clamping assemblies being shown generally at 134a, 134b, 134c, 134d, and 134e. Each of the clamping assemblies is identical in construction and operation, and clamping assembly 134a as mounted to post 130a is illustrated in detail in FIG. 7.

Referring to FIG. 7, clamping assembly 134a includes a substantially cylindrical collar member 136 having a passage 138 therethrough, which is adapted to receive post 130a therein. Passage 138 is dimensioned such that its inner wall is in close tolerance to the outer surface of post 130a. Collar member 136 is longitudinally split throughout its length from the outer surface of collar member 136 inwardly to passage 138. A series of threaded members, such as allen screws or the like shown at 140, 142 and 144 are threadedly engaged in openings formed in the wall of collar member 136 such that threaded members 140-144 bridge the split in collar member 136. With this arrangement, upon turning of threaded members 140-144 in their respective threaded openings, passage 138 in collar member 136 can be expanded or contracted slightly to selectively allow vertical movement of clamping assembly 134a on post 130a.

A lower support plate 146 is welded to the outer surface of collar member 136, and an upper plate 148 is spaced above lower support plate 146 and is also welded to collar member 136. A threaded vertical passage is formed in upper plate 148, and a bolt 150 is threadedly engaged within the passage.

To mount wheel 12 to the fatigue testing apparatus, wheel 12 is first positioned on lower supportedly plate 28, such that plate 28 extends into a recess defined by the lower lip of wheel 12 to engage and support the lower portion of wheel 12 adjacent its lower lip. The lower clamping members, such as shown at 18b, 18c, 18d and 18e are then assembled onto upper member 14 so as to engage the lower lip of wheel 12 and to clamp it against lower supporting plate 28, as previously described. This fixes the vertical and lateral position of the lower lip of wheel 1 during testing. During this procedure, the upper clamping assemblies, such as 134a-134e, are lowered on the posts, such as 130a-130e, so as not to interfere with wheel 12 during clamping of its lower lip against lower supporting plate 28.

After the lower clamping assemblies, such as 18b-18e, are secured against the lower lip of wheel 12, each of the upper clamping assemblies such as 1341a-134e, are moved to their clamping position such as shown in FIG. 7, to firmly secure the upper lip of wheel 12. Referring to clamping assembly 134a as shown in FIG. 7, threaded members 140-144 are turned so as to expand passage 138, and collar member 136 is moved upwardly on post 130a until lower support plate 146 engages the underside of the upper lip of wheel 12. In this position, the outer end of lower support plate 146 engages the rim of wheel 12 adjacent its upper lip. Once this position is attained, threaded members 140-144 are turned in their openings so as to contract passage 138, and to thereby firmly clamp collar member 136 onto post 130a. Bolt 150 is then turned down in the threaded opening formed in the upper plate member 148, to clamp the outer surface of the upper lip of wheel 12 against the upper surfaces of lower support plate 146. This series of steps is repeated for each of the upper clamping assemblies, so that the vertical and lateral position of the upper lip of wheel 12 is fixed during testing.

Clamping of both the upper and lower lips of the wheel during fatigue testing eliminates lateral movement of the lips of wheel 12 which may otherwise occur during testing, and which contributes to inaccurate test results. In this manner, a test most closely replicating operating conditions is achieved.

Various alternatives and embodiments are contemplated as being within the scope of the following claims particularly pointing out and distinctly claiming the subject matter regarded as the invention.

I claim:

1. An apparatus for fatigue testing a vehicle wheel having a pair of spaced lips, comprising:
   a wheel support assembly for maintaining said wheel stationary during testing of said wheel, and including first support means engageable with one side of said wheel inwardly of a first one of said lips, and second support means engageable with the other side of said wheel inwardly of a second one of said lips, said first and second support means cooperating to fix the vertical and lateral position of said wheel on said apparatus during testing; and
   fatigue stress inducing means connectable to said wheel for inducing fatigue stress in said wheel.

2. The apparatus of claim 1, wherein said first wheel support means comprises a wheel supporting plate member onto which said wheel is adapted to be placed.

3. The apparatus of claim 2, wherein said plate member is dimensioned so as to fit within the interior of an outwardly facing recess defined by said first lip.

4. The apparatus of claim 1, wherein said second support means comprises a series of radially spaced clamping assemblies engageable with said wheel adjacent the second lip of said wheel.

5. The apparatus of claim 4, wherein each said clamping assembly comprises a lower support plate engageable with an inner surface of said wheel adjacent said second lip, and a threaded clamping member movable toward and away from said support plate and engageable with an outer surface of said wheel adjacent said second lip.

6. The apparatus of claim 5, wherein said threaded clamping member is threadedly engaged in a threaded opening formed in an upper plate member spaced above said lower support plate, and wherein said second lip of said wheel is adapted to be received in a space disposed between said lower support plate and said upper plate member.

7. The apparatus of claim 4, wherein each said clamping assembly is mounted to a collar member, said collar member being mounted for vertical movement to a post, said collar member being provided with locking means for selectively fixing its vertical position on said post.

8. The apparatus of claim 7, wherein said collar member comprises a substantially cylindrical member including a central passage adapted to receive said post, wherein a wall of said collar member is longitudinally split, and wherein said locking means comprises one or more threaded members threadedly engaged with the wall of said collar member and bridging the split in the wall of said collar member, whereby the passage in said collar member is transversely expandable and contractable to allow selective clamping of said collar member to said post by contraction of said passage.

9. An apparatus for fatigue testing a wheel, having a pair of spaced lips, comprising:
a wheel support assembly for maintaining said wheel stationary, and including a support plate onto which said wheel is placed and adapted to be received within an outwardly facing recess defined by the lower lip of said wheel; and a series of radially spaced clamping assemblies engageable with said wheel adjacent the upper lip of said wheel; said support plate and said clamping assemblies cooperating to fix the vertical and lateral position of the lower and upper portions of said wheel during testing; and
fatigue stress inducing means connectable to said lower support plate for inducing stress in said wheel.

10. An apparatus for fatigue testing a vehicle wheel, comprising:
wheel support means for maintaining said wheel stationary;
a fatigue stress inducing assembly adapted for connection to said wheel and to depend from said wheel, and being operable to induce fatigue stress in said wheel; and
counterweight means for offsetting the weight of said fatigue stress inducing assembly to reduce the effect thereof on said wheel during testing.

11. The apparatus of claim 10, wherein said wheel includes a substantially central opening, and wherein said fatigue stress inducing assembly includes a platte to which said wheel is mountable, and wherein said counterweight means includes means for exerting an upward force on said plate through the opening in said wheel, said upward force offsetting the weight of said fatigue stress inducing assembly.

12. The apparatus of claim 11, wherein a lug is mounted to said plate and extends through the opening in said wheel, and wherein said upward force exerting means exerts the upward force on said plate through said lug.

13. The apparatus of claim 12, wherein said upward force exerting means comprises a piston and rod assembly connected through a flexible connector member to said lug.

* * * * *